United States Patent [19]

Horvath

[11] Patent Number: 4,854,428
[45] Date of Patent: Aug. 8, 1989

[54] DOUBLE-ACTING HYDRAULIC PISTON-AND-CYLINDER DEVICE

[75] Inventor: Eduard Horvath, Wien, Austria

[73] Assignee: Otto Bock Orthopadische Industrie Besitz- und Verwaltungs-KG, Duderstadt, Fed. Rep. of Germany

[21] Appl. No.: 247,896

[22] Filed: Sep. 22, 1988

[30] Foreign Application Priority Data

Sep. 22, 1987 [AT] Austria .................. 2399/87

[51] Int. Cl.$^4$ .................. F16F 9/10; F16F 9/36; F16J 3/04
[52] U.S. Cl. .................. 188/298; 92/41; 188/315; 277/212 FB; 623/18; 623/39
[58] Field of Search ............ 188/298, 314, 315, 322.12, 188/322.16; 623/18, 39, 43, 44, 45; 92/41; 277/212 FB; 267/64.19, 64.23, 64.27

[56] References Cited

U.S. PATENT DOCUMENTS

| | | | |
|---|---|---|---|
| 2,452,885 | 11/1948 | Willard | 188/315 |
| 2,605,474 | 8/1952 | Oliver | 623/44 X |
| 2,651,327 | 9/1953 | Larkin | 92/41 |
| 4,718,680 | 1/1988 | Halconruy et al. | 277/212 FB |

*Primary Examiner*—Robert J. Oberleitner
*Attorney, Agent, or Firm*—Herbert Dubno

[57] ABSTRACT

A double-acting hydraulic piston-and-cylinder unit adapted to constitute a damper for movements in a human joint prosthesis has a boot sealingly connected to the cylinder and the piston rod to receive the hydraulic fluid under pressure as the hydraulic fluid is displaced from one or the other of two cylinder chambers upon displacement of the piston rod. The boot has a conically widening region or segment sealingly secured to the rod and adjoining the cylindrical segment of the boot surrounding the cylinder in a transition segment formed as an outwardly convex bulge and designed to ensure that initial inward movement of the piston rod will give rise to a plate membrane deformation of the elastic boot while only further displacement will result in a rolling action of the membrane. This ensures a generally cylindrical uniform configuration of the boot in all positions of the rod as is essential for effective use in a prosthesis.

5 Claims, 1 Drawing Sheet

DOUBLE-ACTING HYDRAULIC PISTON-AND-CYLINDER DEVICE

FIELD OF INVENTION

My present invention relates to a double-acting hydraulic piston-and-cylinder device or unit, especially for the control of movement in an artificial joint for use in humans, i.e. a joint prosthesis.

More particularly, the invention relates to a unit for the purposes described in which an elastically deformable boot is sealingly connected with the cylinder and with the piston rod, is capable of receiving the hydraulic medium displaced from the cylinder compartments, has a generally cylindrical segment which is sealingly connected to the cylinder, and has a further segment outwardly divergent from the piston rod, sealingly connected thereto, and widening toward the cylindrical segment to which it is connected.

BACKGROUND OF THE INVENTION

Boots of the aforedescribed type have been provided for hydraulic piston-and-cylinder units heretofore in such manner that the generally cylindrical segment of the boot, sometimes referred to as a bellows or cuff even though it need not have accordion-like folds, is directly connected to the widening segment in the region of the upper end of the cylinder, i.e. the end from which the piston rod emerges.

The widening segment in this case extends away from the piston rod at a comparatively small acute angle so that any transition between the widening segment and the cylindrical segment is relatively narrow and can come under excessive stress.

As the piston rod is extended, i.e. extends increasingly from the cylinder during the piston stroke, the angle may become even more acute.

In conventional constructions of such boots, practically the entire volume of the widening region is filled with gas to form a gas cushion with spring-like characteristics. This construction has the drawback that upon retraction of the piston rod and movement of the piston in the cylinder in a direction so as to retract the piston rod, the widening region of the boot is contracted in the form of a rolled membrane and the reduced volume in the interior of the boot must be compensated by a radial yielding thereof. This radial yielding is generally undefined, i.e. the boot distorts in nonuniform and uncontrolled fashion as the result of the presence of the gas cushion.

The outer contours of the boot may then deviate sharply from a cylinder.

This is especially disadvantageous when the device is used in an artificial joint or joint prosthesis for a human subject since, with such prostheses, the available space is limited. The uncontrolled bulging can result in rubbing and rupture of the membrane, rendering the motion-damping unit ineffective.

OBJECTS OF THE INVENTION

It is the principal object of the present invention to provide an improved hydraulic damping unit, especially for a prosthesis, whereby drawbacks of earlier double-acting cylinders with elastic boots can be avoided.

Another object of this invention is to provide an improved double-acting hydraulic piston-and-cylinder unit in which abnormal distortion of the outer contour can be avoided, and, in general, the outer dimensions can be held within limits or can be maintained constant.

SUMMARY OF THE INVENTION

These objects and others which will become apparent hereinafter are attained, in accordance with the present invention in a double-acting piston-and-cylinder hydraulic unit which comprises:

means for forming a cylinder;

a piston axially shiftable in the cylinder and defining therein respective hydraulic-fluid-containing chambers on opposite sides of the piston;

a piston rod connected to the piston and extending axially out of the cylinder;

an elastically deformable boot surrounding the cylinder and the rod while forming therewith a hydraulic-fluid-pressurized variable-volume compartment, the boot having a generally cylindrical segment sealingly connected to the cylinder, a widening segment diverging from and sealingly connected to the rod, and a transition segment connecting the widening segment to the generally cylindrical segment, the transition segment having, in an extended position of the piston rod, an outwardly convex shape and having a greater diameter than that of the generally cylindrical segment, a ratio between the radius (R) of the transition segment at the greater diameter than the generally cylindrical segment and an axial distance (L) between a plane of the transition segment at its greatest diameter and a location closest to the cylinder at which the boot is sealingly connected to the rod being given by the relation:

$$3:1 \geq R/L \geq 1:2;\ \text{and}$$

means for fluid communication between each of the chambers and the variable-volume compartment.

According to the invention, therefore, the transition between the cylindrical segment and the segment widening toward the cylindrical segment of the boot from the piston rod has a bulged shape, i.e. is formed with an annular bulge which, in the extended position of the piston rod, has a greater diameter than the cylindrical segment.

In this embodiment, both the interior of the boot and the chambers of the cylinder to both sides of the piston are completely filled with the hydraulic fluid.

The radius of the annular bulge which is of a greater diameter than the cylinder segment is in a ratio to the axial distance between this greatest diameter and the attachment of the boot to the piston rod of 3:1 to 1:2, preferably 2:1.

This ensures that there is a largest diameter transition portion between the widening segment and the cylindrical segment to guarantee a relatively large angle at the point at which the boot adjoins the rod in all positions of the piston rod.

Moreover, even at the start of retraction or inward movement of the piston rod, the deformation of the membrane constituting the boot is not that of roll membrane with a high displacement volume, but rather a deformation of the bulge within a generally cylindrical outline to stabilize the cylindrical region.

The radial expansion of the cylindrical region is accompanied by an inward movement of the transmission bulge so that the overall diameter of the boot in the fully retracted position of the rod will not be greater than the largest outer diameter of the bulge with the rod fully extended.

The boot thus initially deforms like a plate membrane and only after some substantial deformation, assumes the configuration of a roll membrane.

Advantageously, and according to a feature of the invention, the boot can be formed with a bulge in the region at which the cylindrical segment is affixed to the cylinder, this bulge having a greater diameter than that of the cylindrical segment. This also contributes to a uniform cylindrical shape of the boot in the fully retracted position of the rod. According to another feature of the invention, a region at which the outwardly widening segment of the boot meets the transition region has a greater flexibility than the remainder of the boot. This has been found to be advantageous in providing a transition from plate-membrane to roll-membrane movement and deformation.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figures 1, 2:
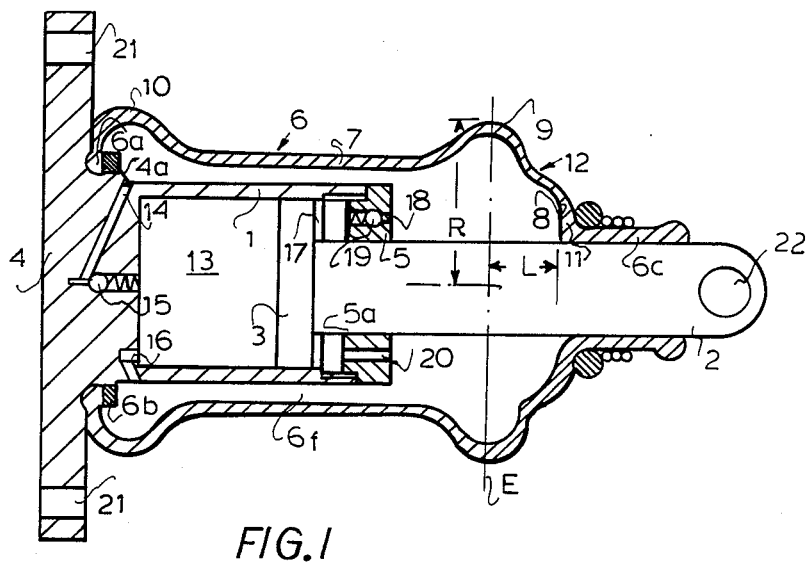
FIG. 1 is an axial cross-sectional view of the unit of the invention with the piston rod extended.
FIG. 2 is an axial cross-sectional view of the unit of the invention with the piston rod fully retracted.

In the drawing, FIG. 1 represents a hydraulic cylinder forming part of a joint prosthesis for human application in which the piston-and-cylinder unit forms a damper.

Within the cylinder 1, a piston 3 is axially displaceable and carries a piston rod 2 which extends axially through the right-hand end of the cylinder. The free end of the rod 2 is provided with a bore 22 for connecting the rod 2 to an actuating member.

At the right-hand end of the cylinder, a cover 5 is provided to close a chamber 17 defined by the piston 3 and this cover, the cover 5 having an axial bore 5a through which the rod 2 passes.

The other end of the cylinder 1 is closed by a mounting flange 4 which is provided with holes 21 enabling it to be bolted to the joint structure.

Surrounding the cylinder 1 and the piston rod 2 is a flexible elastically yieldable boot or bellows 6 which has one end 6a sealingly secured to the cylinder, e.g. by a ring 6b threaded onto a boss 4a of the flange.

At its opposite end, a cylindrical neck 6c is provided to snugly surround the piston rod 2 and is held in place by clamping rings 6d and a guide ring 6e of larger cross section defining the deformation pattern of the portion 11 of the boot meeting the piston rod 2 closest to the cylinder.

The boot 6 thus has a cylindrical segment 7 and a segment 8 widening away from the piston rod 2 toward the segment 7.

In a transition region between the cylindrical segment 7 and the widening segment 8, the boot 6 is provided with a transition segment 9 of larger diameter than the cylindrical segment and which generally is outwardly convex in the form of a bulge as shown in FIG. 1 when the rod 2 is fully extended from the cylinder.

At the end of the cylindrical segment 7 opposite that at the bulge 6 is provided, i.e. the end proximal to the attachment of the boot to the cylinder, the boot is provided with a further bulge 10 which also has a greater diameter than the cylindrical segment. The chamber of the bulge 10 can be equal to that of the bulge 9 in the fully extended position of the rod.

The widening segment 8 can have a conicity such that the radius R of the transition region 9, which has a greater diameter than that of the cylindrical segment 7, is about twice the distance L between the median plane E perpendicular to the axis and through the region 9 of largest diameter from the region 11 at which the boot engages the rod.

Between the region 9 of greater diameter and the widening segment 8 of the boot, the latter is provided with a region 12 of greater flexibility than elsewhere along the elastically deformable boot. This region is the region in which the boot has the function of a plate membrane and the plate membrane deformation deforms at the beginning of the inward movement of the rod 3.

The interior of the boot 6 is connected to the cylinder chamber 13 defined between the piston 3 and the flange 4, by a connecting passage 14 in which a check valve 15 is provided to prevent the flow of hydraulic fluid from the cylinder chamber 13 into the compartment 6f of the boot communication between chamber 13 and compartment 6f is permitted by a throttle 16.

The hydraulic chamber 17 above the piston 3 develops a negative pressure upon inward displacement of the piston rod (compare FIGS. 1 and 2), so that hydraulic fluid is drawn from the hydraulic-fluid-filled space 6f through the throttle 20 and through a passage 18 provided with a check valve 19 preventing outflow of fluid from the chamber 17 into the boot.

Since the volume of hydraulic fluid driven out of the cylinder chamber 13 is greater than that drawn into the cylinder chamber 17 by inward movement of the piston rod and at the same time there is a reduction in the distance L because of the inward movement of the piston rod and the volume of the space within the widening segment of the boot, the cylindrical segment 7 radially widens in the manner illustrated in FIG. 2.

During this movement, the widening segment 8 initially deforms like a membrane disk or plate which is to say that it first flattens to become approximately planar, parallel to the plane E as the right-hand end of the boot is thrust to the left. Thereafter, the transition portion 9 of the boot rolls around the ring 6e as the region 11 passes the plane E so that the transition region 9 then moves inwardly. The final position of this transition region has been designated at 9 in FIG. 2.

When the piston 3 is again displaced to the right to extend the piston rod 2 from the cylinder, the hydraulic flow is in the opposite direction. Hydraulic fluid from the interior of the boot 6 enters via the passage 14 past the check valve 15 and partly via the throttle 16 into the cylinder chamber 13 below the piston 3. Simultaneously, hydraulic fluid from the hydraulic chamber 17 can be driven out through the throttle 20 into the interior of the boot.

Since the volume of hydraulic fluid drawn into the cylinder is greater than that displaced therefrom, the volume of hydraulic fluid in the compartment 6f is reduced by the outward movement of the piston rod. The cylindrical segment 7 uniformly constricts back to this original position as shown in FIG. 1, whereupon the bulges 9 and 10 form again. The fully extended position, of course, has been illustrated in FIG. 1.

I claim:

1. A double-acting piston-and-cylinder hydraulic unit which comprises:

means for forming a cylinder;

a piston axially shiftable in said cylinder and defining therein respective hydraulic-fluid-containing chambers on opposite sides of said piston;

a piston rod connected to said piston and extending axially out of said cylinder;

an elastically deformable boot surrounding said cylinder and said rod while forming therewith a hydraulic-fluid-pressurized variable-volume compartment, said boot having a generally cylindrical segment sealingly connected to said cylinder, an outwardly widening segment diverging from and sealingly connected to said rod, and a transition segment connecting said widening segment to said generally cylindrical segment, said transition segment having, in an extended position of said piston rod, an outwardly convex shape and having a greater diameter than that of said generally cylindrical segment, a ratio between the radius (R) of said transition segment at said greater diameter than said generally cylindrical segment and an axial distance (L) between a plane of said transition segment at its greatest diameter and a location closest to said cylinder at which said boot is sealingly connected to said rod being given by the relation:

$$3:1 \geq R/L \geq 1:2;\ \text{and}$$

means for fluid communication between each of said chambers and said variable-volume compartment.

2. The double-acting piston-and-cylinder hydraulic unit defined in claim 1 wherein said ratio R/L is substantially 2:1.

3. The double-acting piston-and-cylinder hydraulic unit defined in claim 1 wherein said transition segment forms an outward annular bulge of said boot in said extended position of said rod.

4. The double-acting piston-and-cylinder hydraulic unit defined in claim 1 wherein said boot is formed at a junction between said transition segment and said outwardly widening segment with a region of greater flexibility than the remainder of said boot.

5. The double-acting piston-and-cylinder hydraulic unit defined in claim 1 wherein said boot is formed proximal to its sealing connection to said cylinder with an outward annular bulge having a diameter greater than that of said generally cylindrical segment in said extended position of said rod.

* * * * *